(12) United States Patent
Vaccaro et al.

(10) Patent No.: US 7,357,014 B2
(45) Date of Patent: *Apr. 15, 2008

(54) POROSITY REFERENCE STANDARD UTILIZING ONE OR MORE DISCRETE WIRES

(75) Inventors: Christopher M. Vaccaro, Ofallon, MO (US); April L. Beisiegel, Freeburg, IL (US); David A. Lilienthal, Kent, WA (US)

(73) Assignee: The Boeing Company, Chicago, IL (US)

( * ) Notice: Subject to any disclaimer, the term of this patent is extended or adjusted under 35 U.S.C. 154(b) by 176 days.

This patent is subject to a terminal disclaimer.

(21) Appl. No.: 11/288,591

(22) Filed: Nov. 29, 2005

(65) Prior Publication Data

US 2007/0119256 A1    May 31, 2007

(51) Int. Cl.
*G01N 29/30* (2006.01)
(52) U.S. Cl. ..................................................... 73/1.86
(58) Field of Classification Search ................. 73/1.82, 73/1.86
See application file for complete search history.

(56) References Cited

U.S. PATENT DOCUMENTS 4,406,153 A * 9/1983 Ophir et al. ................. 73/1.86
5,196,343 A * 3/1993 Zerhouni et al. .............. 436/8
7,216,544 B2   5/2007 Vaccaro et al.

OTHER PUBLICATIONS

Pending patent application, filed on Oct. 20, 2005 inventor Christopher M. Vaccaro, Ultrasonic Inspection Reference Standard for Porous Composite Materials (26 pages), U.S. Appl. No. 11/254,464.
Pending patent application, filed on Nov. 17, 2005, first named inventor, Christopher M. Vaccaro, Porosity Standard Utilizing a Mesh (25 pages), U.S. Appl. No. 11/281,111.

* cited by examiner

*Primary Examiner*—John E. Chapman
(74) *Attorney, Agent, or Firm*—Timothy K. Klintworth (57) ABSTRACT

The invention relates to pseudo porosity standards, and methods for their manufacture and use, which may substantially mimic the effect porosity has on ultrasonic sound as it passes through a composite laminate. An ultrasonic inspection reference standard for composite materials having porosity may include a member having at least one thickness and at least one discrete wire. The member may be manufactured from a fiber-free polymer resin using a stereo lithography process. The discrete wire may scatter and attenuate ultrasonic energy. The reference standard may replace more costly, porous, fiber-reinforced, composite reference standards in the aircraft industry and in other non-aircraft applications.

21 Claims, 6 Drawing Sheets

POROSITY REFERENCE STANDARD UTILIZING ONE OR MORE DISCRETE WIRES

CROSS-REFERENCE TO RELATED APPLICATIONS

This application hereby incorporates by reference U.S. application Ser. No. 11/090,553, filed on Mar. 25, 2005, and titled Ultrasonic Inspection Reference Standard For Composite Materials.

BACKGROUND OF THE INVENTION

Composite laminate reference standards are employed when performing ultrasonic inspection of composite laminate materials. They are used to aid in the detection of planar defects such as delaminations, foreign material, and the detection and quantification of porosity. A relationship exists between the strength of a composite laminate and the presence of defect conditions. This relationship is established in the course of effects-of-defects programs that look at the strength degradation of materials as a result of defects. Composite reference standards are currently manufactured with representative planar conditions to aid in the detection of delaminations and foreign material. It is difficult however to tie detection and quantification of porosity to a representative planar defect reference standard without the introduction of defects that mimic porosity.

Due to this difficulty, one approach to detecting and quantifying porosity in composite laminates has been to build a set of porosity reference standards for a given material. This set of standards, which are costly to build and certify for use, are used to qualify production inspection systems and are used to determine the operating characteristics of ultrasonic inspection systems. The introduction of new composite materials and the cost associated with qualifying new and existing ultrasonic inspection systems to inspect those materials has produced a need to build and qualify less expensive porosity standards. The standards, once produced, can be tied back to material properties via effects-of-defects programs and used to evaluate the strength characteristics of the materials being inspected.

SUMMARY OF THE INVENTION

In one aspect of the invention, an ultrasonic inspection reference standard for composite materials having porosity comprises a member having at least one thickness and at least one discrete wire. The member is manufactured from a fiber-free polymer resin.

In another aspect of the invention, an ultrasonic inspection reference standard for composite materials having porosity comprises a member having at least one thickness and at least one discrete wire. The reference standard is adapted to contain at least one of the acceptable and respectable ultrasonic properties of a fiber-reinforced composite part having porosity.

In a further aspect of the invention, an ultrasonic inspection process for composite materials having porosity is provided. A reference standard is manufactured. The reference standard comprises a member having at least one thickness and at least one discrete wire. A fiber-reinforced composite part having porosity is inspected with an ultrasonic technique using the reference standard.

These and other features, aspects and advantages of the invention will become better understood with reference to the following drawings, description and claims.

DETAILED DESCRIPTION OF THE INVENTION

The following detailed description is of the best currently contemplated modes of carrying out the invention. The description is not to be taken in a limiting sense, but is made merely for the purpose of illustrating the general principles of the invention, since the scope of the invention is best defined by the appended claims.

Figure 1:
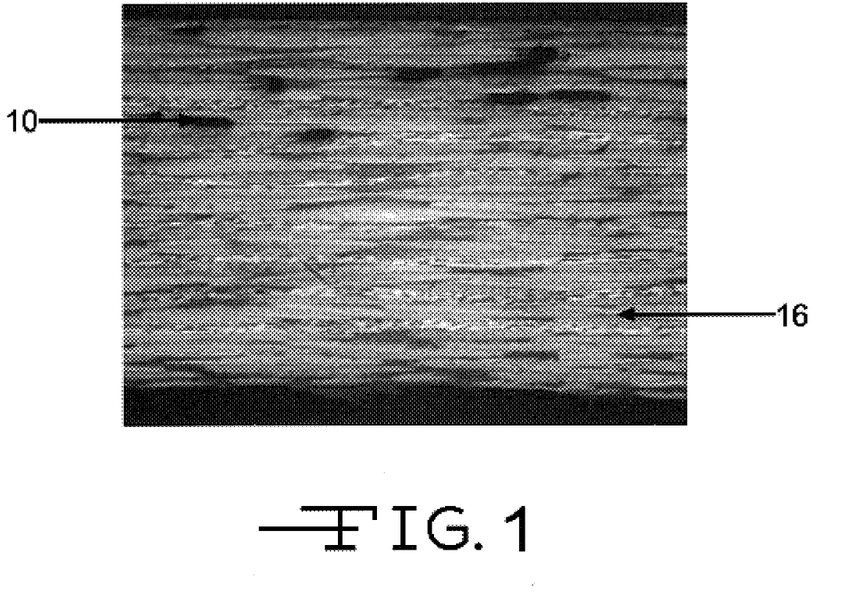
FIG. 1 is a photomicrograph of a composite laminate with porosity.
Figure 2:
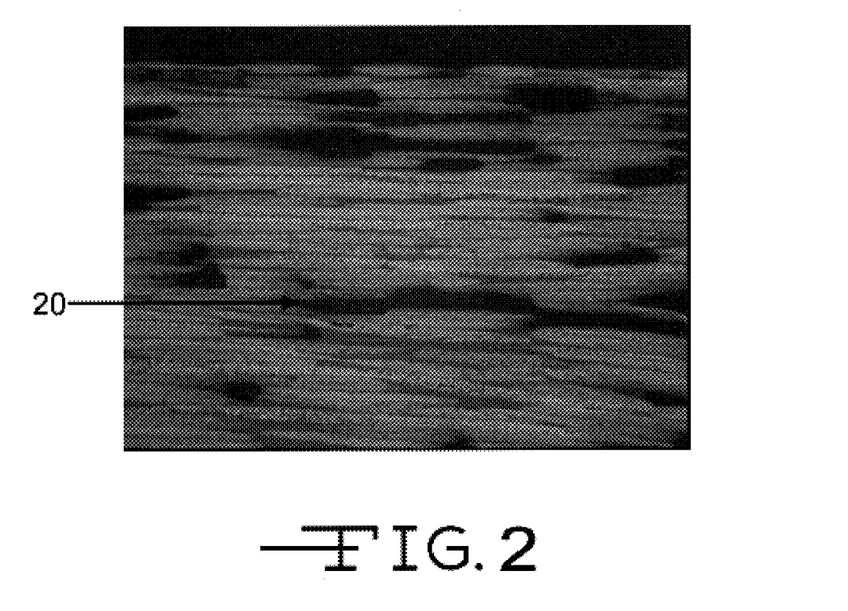
FIG. 2 is a photomicrograph of a composite laminate with large, planer-like porosity.

Composite laminates consist of two primary constituents including a fiber, and a resin matrix that bonds the fibers together. The fiber is typically graphite. Porosity in composite laminates is an unwanted product of the manufacturing cure cycle and is characterized by voids or a lack of resin within the laminate. FIG. 1 depicts a photomicrograph of a composite laminate with areas of porosity 10 shown as elliptical shapes that appear darker than the surrounding non-porous areas 16. The morphology and distribution of the porosity vary depending on a number of processing variables. The size of porosity also varies from relatively small diameters of 0.005" up to large planar conditions 20 like those illustrated in FIG. 2.

Figure 3:
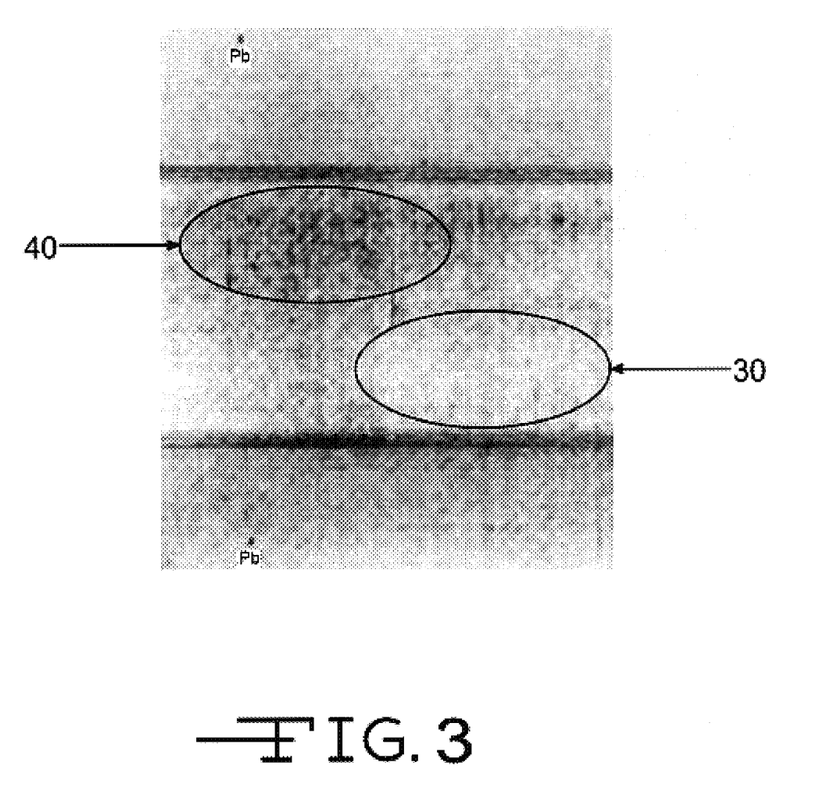
FIG. 3 is an ultrasonic C-scan of a composite laminate with porosity.

Porosity within a composite laminate may be quantitatively measured using high frequency ultrasonic methods. As the void content of a laminate increases, so does the ultrasonic attenuation. Ultrasonic attenuation is the combined loss of acoustic energy within the laminate which results from reflection and scattering of the sound pulse as it passes through the laminate. The ultrasonic C-scan in FIG. 3 illustrates this condition. The light gray areas 30 are where there is very little to no porosity in the laminate. The dark areas 40 are where the laminate has porosity of some level.

Previous work has shown that photo-polymer resins used in stereo lithography (SLA), as well as conventional thermos set and thermoplastic resins like those used to bind fibers in composite laminates, have similar ultrasonic (acoustic) properties to graphite epoxy composite laminates. This is detailed in U.S. application Ser. No. 11/090,553, filed on Mar. 25, 2005, and titled Ultrasonic Inspection Reference Standard For Composite Materials, which is hereby incorporated by reference.

Figure 4:
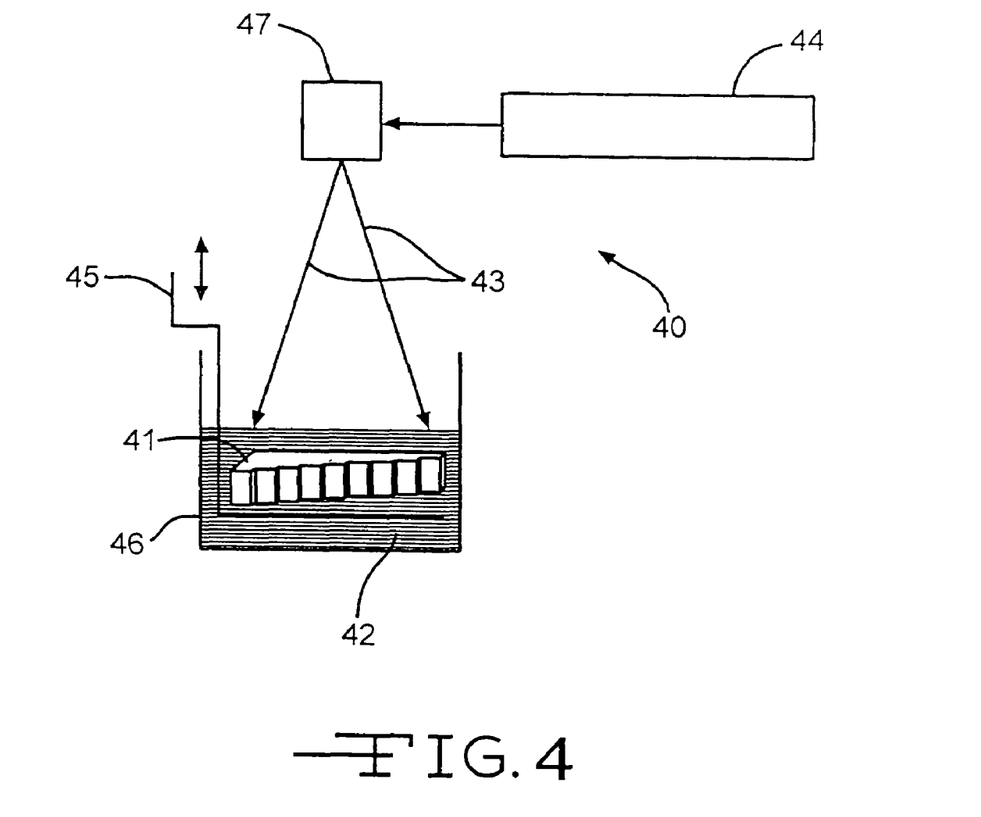
FIG. 4 is a front view of a stereo lithography process.

As shown in FIG. 4, the use of a stereo lithography process may produce plastic parts 41, such as an ultrasonic inspection reference standard manufactured from a photo-polymer resin, directly from a 3D CAD (computer-aided design) model. The surface of a liquid photopolymer 42 is solidified layer-by-layer using a laser beam 43 emitted by a laser 44. When the laser beam 43 hits the liquid photopolymer 42, it solidifies the resin. When a layer is fully traced, a movable table 45 is then lowered in the vat 46 of resin. A scanner system 47 directs the laser beam 43 according to a loaded CAD model. The self-adhesive property of the material causes the layers to stick with each other and in this way a three-dimensional part 41 is formed in multi-layers. The stereo lithography process is accurate and suitable for smooth surface finished parts and may be used for rapid prototyping. Parts manufactured using the stereo lithography process may be used for conceptual designs, product verification, and pattern making. Use of the stereo lithography process may enable the manufacture of ultrasonic inspection reference standards, such as a polymer resin reference standard, with varying thicknesses and geometries that resemble the fiber-reinforced part to be inspected. The method of manufacturing an ultrasonic inspection reference standard from a fiber-free polymer resin may not require any tooling, and is not limited to the methods discussed.

To demonstrate the use of a fiber-free photo-polymer resin as a reference standard, a photo-polymer resin reference standard was manufactured in substantially the same configuration as a prior art graphite-epoxy reference standard by using the stereo lithography process shown in FIG. 4. Both standards were then ultrasonic ally scanned at 5.0 MHz using both the through-transmission technique and the pulse-echo technique. The data obtained when using the through-transmission technique is illustrated in the x-y plot 50 of FIG. 5, while the data obtained when using the pulse-echo technique is illustrated in the x-y plot 60 of FIG. 6. The plots 50 and 60 demonstrate attenuation 52 and 62 measured in decibels (dB) versus thickness 51 and 61 measured in inches. The attenuation is a decrease in intensity of a sound wave as a result of absorption and scattering of ultrasonic energy. The plots 50 and 60 include data points 53 and 63 representing a photo-polymer resin reference standard free of fibers, and data points 54 and 64 representing a prior art graphite-epoxy reference standard.

Figure 5:
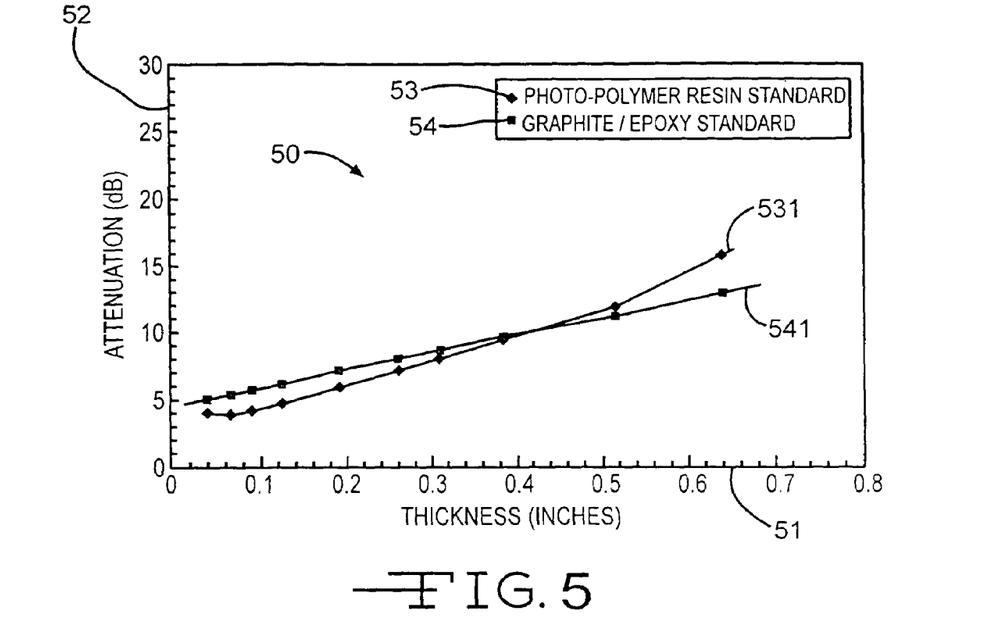
FIG. 5 is an x-y plot showing attenuation versus thickness when applying through-transmission technique to both a photo-polymer resin standard and a graphite-epoxy standard.
Figure 6:
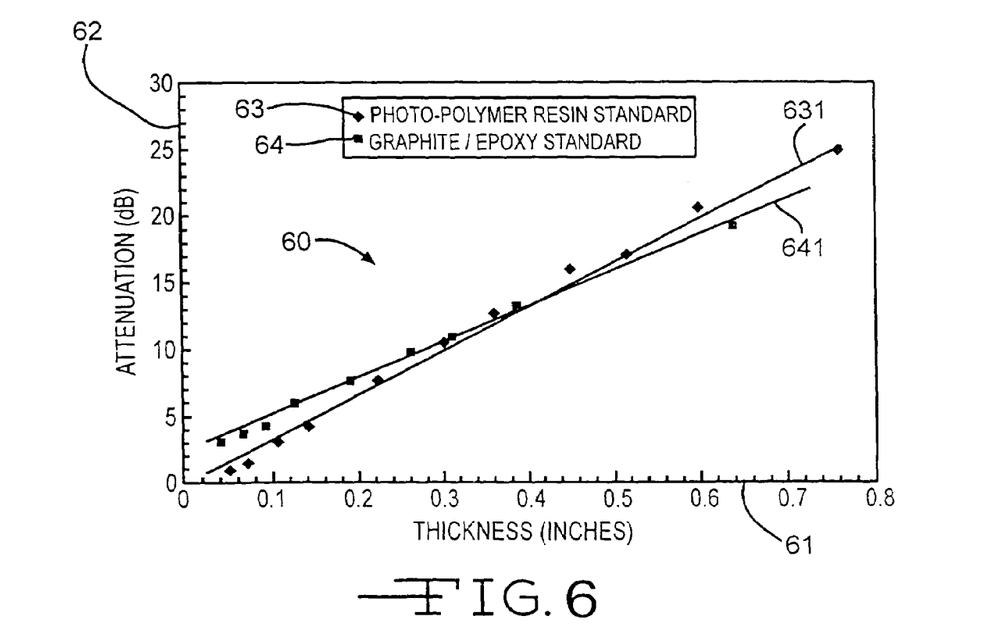
FIG. 6 is an x-y plot showing attenuation versus thickness when applying pulse-echo technique to both a photo-polymer resin standard and a graphite-epoxy standard.

As shown in FIGS. 5 and 6, the slopes 531 and 631 of the photo-polymer resin standard are steeper than the slopes 541 and 641 of the prior art graphite-epoxy reference standard. However, the results are within the system noise, which is typically +/−2 dB. Consequently, the prior art graphite-epoxy reference standard may be substituted with the fiber-free photo-polymer resin reference standard. Since ultrasonic attenuation is material dependent, the thickness of the polymer resin reference standard may be altered to bring the slopes 531, 541, 631, and 641 in line if needed. Using this approach, a fiber-free polymer resin reference standard may be designed to have an equivalent thickness based on the material properties of the fiber-reinforced composite part to be tested rather than the actual thickness of a prior art fiber-reinforced composite reference standard.

The present invention relates to pseudo porosity standards, and methods for their manufacture and use, which substantially mimic the effect porosity has on ultrasonic sound as it passes through a composite laminate. In an embodiment of the invention, as discussed in more detail below, a pseudo porosity standard may be manufactured using stereo lithography on a polymer resin to make a member having at least one thickness which displays similar acoustic properties of the composite laminate (fiber/resin combination). At least one discrete wire may be incorporated into the member to produce a standard which transmits ultrasonic energy, with the discrete wire acting to scatter and attenuate the energy. For purposes of this application, the term discrete wire is defined as a separate and independent wire. As such, this application is not directed towards and does not include the use of a wire mesh, made up of an interwoven weave of wires, which is being claimed in a separately filed application. The discrete wire may be made of metallic and non-metallic materials. In other embodiments, varying types of wire may be used, and varying types of fiber-free polymer resin may be utilized, including the use of a polymer resin which is substantially similar to the resin of a composite material to be inspected. In still other embodiments, a non-stereo lithography process may be applied.

Figure 7:
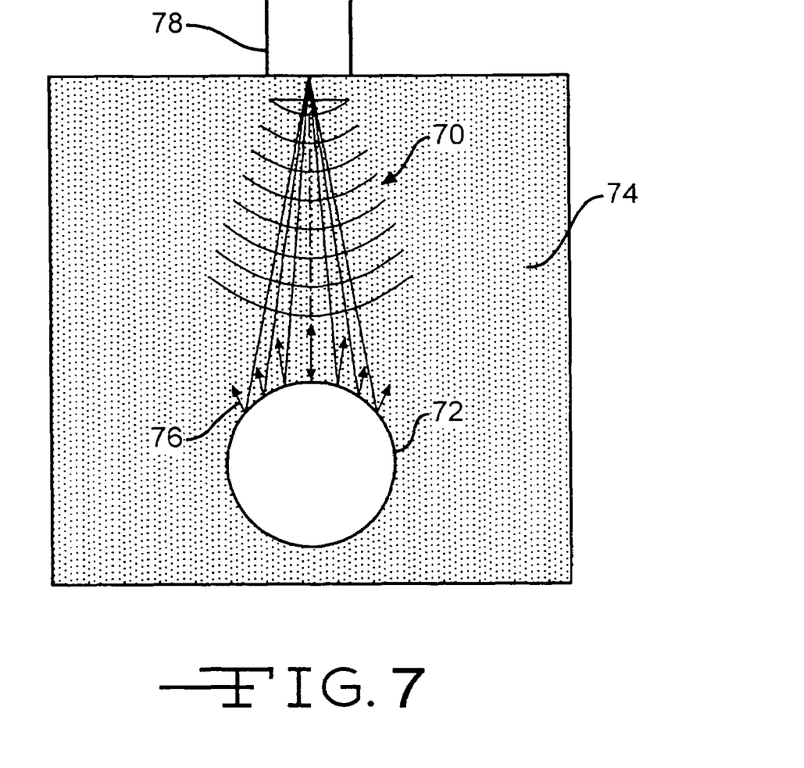
FIG. 7 is a simplified illustration of the ultrasonic two dimensional scattering which occurs off a circle.
Figure 8:
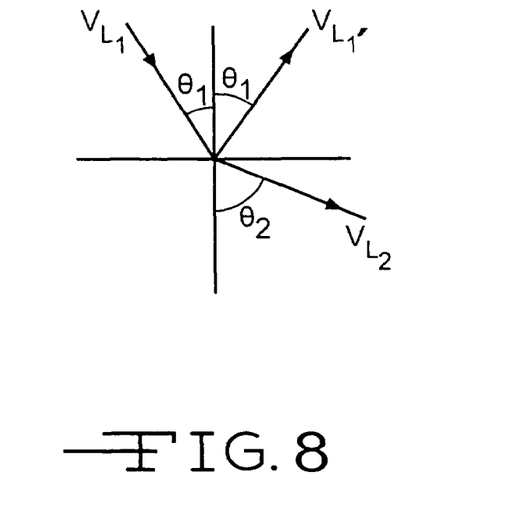
FIG. 8 depicts the principle of reflection and scattering under Snell's law.

The invention was arrived at in part due to the discovery that scattering of an ultrasonic pulse of energy can be produced through the placement of small voids within a homogeneous median. This is the general principle for producing voids (porosity) within a composite laminate. Similarly, it was discovered that scattering can be accomplished through the introduction of hollow shafts in a homogeneous median. The amount of ultrasonic scatter is dependent, in part, on the size of the shafts, the number of shafts, and their proximity to one another. FIG. 7 is a simplified illustration of the ultrasonic two dimensional scattering 70 which may occur off a circle 72. In this example, the acoustic impedance mismatch between the base material 74, in this case a homogeneous median, and the hollow circle 72 may be large. This may produce nearly 100 percent reflection 76 of the incident ultrasonic ray perpendicular to the ultrasonic transducer 78. As shown in FIG. 8, the principle of reflection and subsequent scattering is based on Snell's law as follows:

$$\frac{\sin\theta_1}{V_{L_1}} = \frac{\sin\theta_2}{V_{L_2}}$$

Snell's law provides the well-known relationship between angles of incidence and refraction for a wave impinging on an interface between two media with different indices of refraction. The law follows from the boundary condition that a wave be continuous across a boundary, which requires that the phase of the wave be constant on any given plane, resulting in $n_1 \sin \theta_1 = n_2 \sin \theta_2$, where $\theta_1$ and $\theta_2$ are the angles from the normal of the incident and refracted waves, respectively.

This same principle of scattering off a hollow shaft in two dimensions can be extrapolated to ultrasonic scattering off one or more discrete wires which will produce three dimensional scattering. Generally, porosity produced in composite laminates may be discrete, or may acquire columnar shapes. Because graphite epoxy laminates may consist of isotropic plies (0, 90, +45 and −45 degree plies), columnar voids may occur in any direction. Through the introduction of one or more discrete wires, ultrasonic attenuation can be produced. The discrete wire, which may mimic columnar porosity, may be comprised of numerous arcs for the ultrasonic energy to scatter from which may result in scattering similar to that shown in the example of FIG. 7. The discrete wire may be of any size or material, and may utilize circumferential shapes to produce the desired scattering.

To use discrete wire as a scattering device, the one or more discrete wires may be molded or inserted into a median that has similar acoustic properties of graphite epoxy. This may be accomplished by manufacturing a member out of a photopolymer resin using the SLA process. One or more narrow shafts, comprising openings or holes, of uncured resin may be produced in the member during the SLA process. The width of the shafts may approach the diameter or thickness of the discrete wire chosen for the application. In other embodiments, the shafts may comprise varying sizes, orientations, and configurations. The discrete wire may be inserted into the uncured resin shafts produced during the SLA process, with each discrete wire being inserted into a separate respective uncured resin shaft. The member may then be subjected to a final ultraviolet cure to advance the cure of the pre-cured resin as well as to cure the uncured resin around the discrete wire to secure it in place against or within the member. At least one of the diameter, location, material, spacing, and type of the discrete wire may be chosen to achieve equivalent ultrasonic attenuation of porosity for a graphite epoxy composite laminate.

In one embodiment of the invention, an ultrasonic inspection process may start with designing and building a three-dimensional model of the standard, according to a porous, fiber-reinforced composite part to be inspected. The porous, fiber-reinforced composite part to be inspected may comprise a graphite epoxy composite material having porosity. The three-dimensional model may be designed to include at least one shaft to accommodate at least one discrete wire at one or more locations where the resin will be uncured. The model may include a plurality of spaced apart shafts, each adapted to receive a separate, discrete wire. At least one of the number, configuration, spacing, type, and size of one or more shafts, and/or at least one of the type, location, number, size, spacing, and diameter of one or more discrete wires may be predetermined prior to manufacture of the standard in order to provide the standard with at least one of the acceptable and rejectable ultrasonic properties of the porous composite part to be inspected. In such manner, the designed reference standard may comprise substantially the ultrasonic properties of a fiber-reinforced composite reference standard. The one or more shafts may be designed to be located in a variety of locations on or within the model. At other non-shaft locations, the model may be designed to have solid surfaces where the resin will be cured using the SLA process. The model, which may be arrived at using computer-aided-drafting, may be loaded into a stereo lithography machine to manufacture the reference standard by curing a photopolymer resin with a laser. In other embodiments, varying types of resins, such as a fiber-free polymer resin, and varying types of processes may be used to manufacture the standard.

In curing the photopolymer resin, the laser may raster back and forth curing resin only in the areas where the model indicates material to be. The areas which are designated to contain one or more shafts, as dictated by the model, may not be cured by the laser during the SLA process. In these areas, the resin may remain uncured and un-purged so that it may later be used to bond against one or more discrete wires. The SLA process may result in a member having at least one thickness. The member may comprise any shape, configuration, or thickness. The thickness of the member may be a substantially equivalent thickness based on the material properties of the composite material to be inspected. As the member is being built up during the SLA process, at least one shaft of uncured resin at the designated areas of the member may be formed in accordance with the positioning of the shafts of the model. After the areas around the one or more shafts are formed in the member, at least one discrete wire may be inserted into one or more shafts to allow the uncured resin to flow around the wire. Each discrete wire may be inserted into a separate spaced apart shaft. The shafts may be located in a variety of locations against or within the member. The SLA process may be continued to encase the discrete wire in place against or within one or more shafts of the member. When the SLA process is finished, the standard may be given a post UV cure to harden the resin and complete manufacture of the standard.

The process may produce an ultrasonic reference standard, made of a fiber-free polymer resin member, containing at least one discrete wire. The manufactured standard may substantially mimic the ultrasonic properties of a porous composite material, allowing the replacement of fiber-reinforced composite reference standards. A varying amount of attenuation, or porosity, may be produced in the standard to accomplish the desired ultrasonic reference standard.

Figure 9:
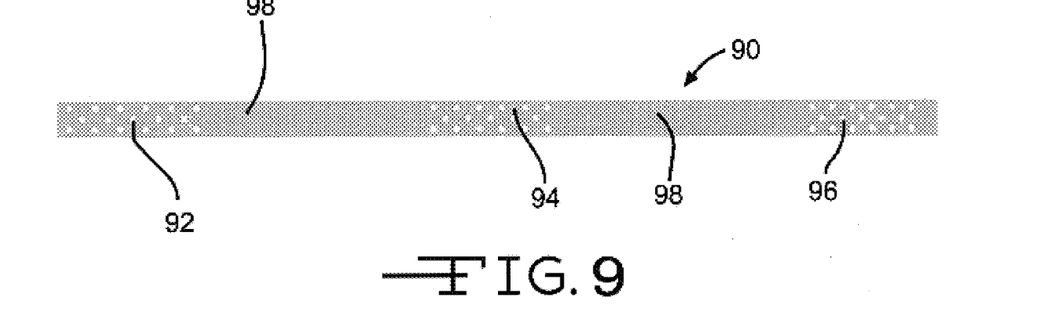
FIG. 9 is a side view of a 3D model to aide in illustrating the ultrasonic effects of placing discrete wires varying distances apart under the invention.
Figure 10:
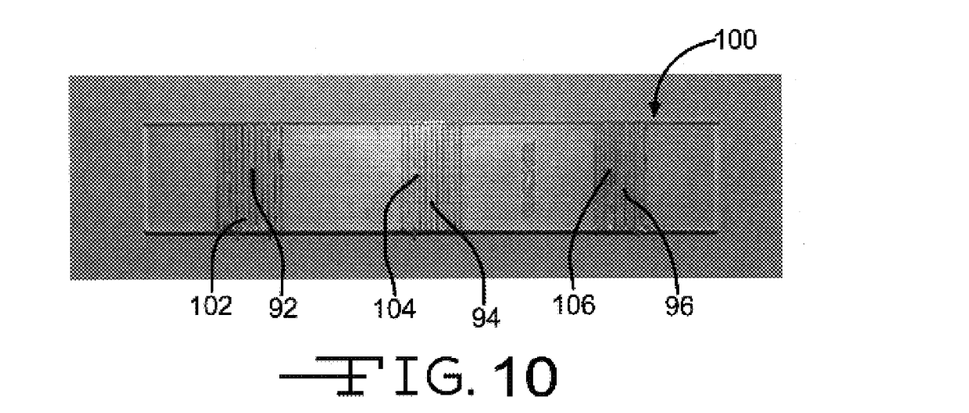
FIG. 10 depicts a top view of a cured index standard manufactured under the invention in accordance with the model of FIG. 9.

FIG. 9 is a side view of a 3D model 90 to aide in illustrating the ultrasonic effects of placing discrete wires varying distances apart under the invention. The model 90 is designed to have horizontally extending shafts at each of locations 92, 94, and 96. At location 92, the shafts are designed to be spaced apart horizontally 4.5D, which comprises four-and-a-half times the diameter of the wire D to be run within the shafts. At location 94, the shafts are designed to be spaced apart horizontally 4.0D, which comprises four times the diameter of the wire D to be run within the shafts. At location 96, the shafts are designed to be spaced apart horizontally 3.5D, which comprises three-and-a-half times the diameter of the wire D to be run within the shafts. FIG. 10 depicts a top view of a cured index standard 100 manufactured under the invention in accordance with the model of FIG. 9. As governed by the model, the wires 102 at location 92 are spaced apart horizontally 4.5D, the wires 104 at location 94 are spaced apart horizontally 4.0D, and the wires 106 at location 96 are spaced apart horizontally 3.5D.

Figure 11:
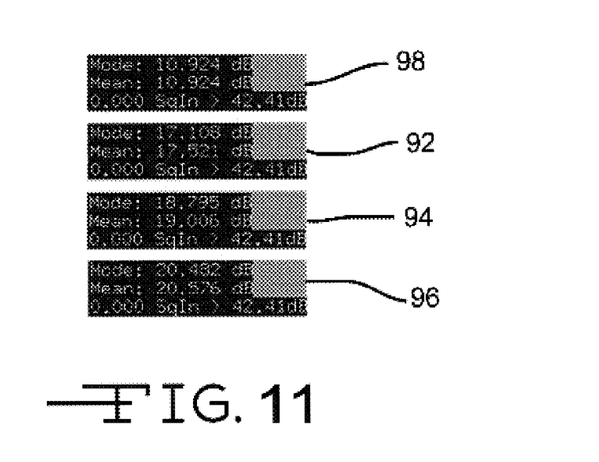
FIG. 11 shows the ultrasonic scan results obtained when the index standard of FIG. 10 was ultrasonic ally scanned at 5.0 MHz.

FIG. 11 depicts the histogram values of the ultrasonic scan results obtained when the index standard of FIG. 10 was ultrasonic ally scanned at 5.0 MHz. The amplitude response of the through-transmission signal was measured in decibels at locations 92, 94, and 96 in FIG. 10, and compared against the amplitude response of the base material 98 of FIG. 10, which comprises the area where the wires do not exist. Subtraction of the histogram values in locations 92, 94, and 96 from the base material 98 histogram values reveal the varying ultrasonic attenuation which may achieved by varying the distance of the wire placement. For instance, in this example, after subtracting the base 98 attenuation value, location 92 had an attenuation value of 6.184 dB (17.108 dB−10.924 dB=6.184 dB); after subtracting the base 98 attenuation value, location 94 had an attenuation value of 7.871 dB (18.795 dB−10.924 dB=7.871 dB); and after subtracting the base 98 attenuation value, location 96 had an attenuation value of 9.558 dB (20.482 dB−10.924 dB=9.558 dB). The results demonstrate that varying the spaced apart distance of the discrete wires may have a direct effect on attenuation.

Index standards manufactured under the invention may be used to inspect a fiber-reinforced composite part having porosity using an ultrasonic technique. For instance, the manufactured standard may be ultrasonic ally scanned using ultrasonic inspection, such as pulse-echo and through-transmission. A porous, fiber-reinforced composite part may be ultrasonically scanned using the same technique. The data obtained from scanning the porous, fiber-reinforced composite part may be compared with the data obtained from scanning the manufactured standard. Based on the data, a decision may be made as to whether to accept or reject the composite part.

By using the combination of a fiber-free polymer resin member and at least one discrete wire, the reference standard may be manufactured at lower manufacturing cost, may be manufactured in less time, and may be manufactured using a method that does not require any tooling, as compared to many existing fiber-reinforced composite reference standards. The manufactured ultrasonic inspection reference standard may substantially comprise the ultrasonic properties of a graphite-epoxy reference standard, or other type of reference standard made of varying materials. In such manner, the manufactured ultrasonic inspection reference standard may replace a graphite-epoxy reference standard, or other type of fiber-reinforced reference standard.

Using stereo lithography to produce shafts adapted to contain at least one discrete, pre-determined wire in a solid median member may be of value because manufacturing costs may be roughly ten percent of the traditional cost of manufacturing composite standards with similar porosity. The ability to produce shafts adapted to receive discrete, pre-determined wires in particular patterns to mimic naturally occurring conditions may make this approach desirable in the manufacturing of pseudo porosity standards. The nature of the manufacturing process, including its tailor ability and repeatability, may enable the production of multiple reference standards having substantially equivalent acoustic properties which may allow inspection of porous, composite parts around the world. In such manner, the cost of manufacturing and certification of reference standards may be reduced. The process may become the foundation for the development of pseudo porosity standards to characterize ultrasonic equipment, and may replace current composite reference standards, such as graphite-epoxy reference standards. The invention may be used for ultrasonic inspection of porous, composite parts used in the aircraft industry, both commercial and defense, and in other non-aircraft applications.

It should be understood, of course, that the foregoing relates to exemplary embodiments of the invention and that modifications may be made without departing from the spirit and scope of the invention as set forth in the following claims.

We claim:

1. An ultrasonic inspection reference standard for composite materials having porosity, comprising: a member having at least one thickness, wherein said member is manufactured from a fiber-free photo-polymer resin; and a plurality of spaced-apart discrete wires disposed within or against the member.

2. The ultrasonic inspection reference standard of claim 1, wherein said photo-polymer resin comprises substantially similar ultrasonic properties of a composite material.

3. The ultrasonic inspection reference standard of claim 1, wherein said member comprises more than one thickness.

4. The ultrasonic inspection reference standard of claim 1, wherein said member is created using a 3D computer-aided-design model.

5. The ultrasonic inspection reference standard of claim 1, wherein said at least one thickness of said member comprises substantially similar ultrasonic properties of a thickness of a composite material.

6. The ultrasonic inspection reference standard of claim 1, wherein said member is manufactured using a stereo lithography process.

7. The ultrasonic inspection reference standard of claim 1, wherein said reference standard comprises substantially similar ultrasonic properties of a composite material having porosity.

8. The ultrasonic inspection reference standard of claim 7, wherein one or more of the type, diameter, location, size, and spacing of said plurality of spaced-apart discrete wires provides the ultrasonic inspection reference standard with substantially similar ultrasonic properties of a composite material having porosity.

9. The ultrasonic inspection reference standard of claim 1, wherein said ultrasonic reference standard is for graphite epoxy composite materials having porosity.

10. The ultrasonic inspection reference standard of claim 1, wherein said member is defined by a plurality of shafts in which said plurality of spaced-apart discrete wires are positioned.

11. The ultrasonic inspection reference standard of claim 1, wherein said plurality of spaced-apart discrete wires are unconnected.

12. The ultrasonic inspection reference standard of claim 11, wherein said member is defined by a plurality of internal shafts in which said plurality of unconnected, spaced-apart discrete wires are disposed.

13. The ultrasonic inspection reference standard of claim 11, wherein one or more of the type, location, diameter, and spacing of said plurality of unconnected, discrete spaced-apart wires provides said reference standard with substantially similar ultrasonic properties of a composite material having porosity.

14. The ultrasonic inspection reference standard of claim 1, wherein said reference standard is for the inspection of a fiber-reinforced composite part of an aircraft structure.

15. An ultrasonic inspection reference standard for composite materials having porosity, comprising: a member having at least one thickness, wherein said member was manufactured using a stereo lithography process; and a plurality of spaced-apart discrete wires disposed within or against the member, wherein said reference standard has substantially similar ultrasonic properties of a fiber-reinforced composite part having porosity.

16. The ultrasonic inspection reference standard of claim 15, wherein said member is manufactured from a fiber-free polymer resin.

17. The ultrasonic inspection reference standard of claim 15, wherein said member is defined by a plurality of shafts in which said plurality of spaced-apart discrete wires are disposed.

18. The ultrasonic inspection reference standard of claim 17, wherein one or more of the type, location, diameter, and spacing of said plurality of spaced-apart discrete wires provides said reference standard with substantially similar ultrasonic properties of a composite part having porosity.

19. The ultrasonic inspection reference standard of claim 15, wherein said reference standard contains the ultrasonic properties of a graphite-epoxy reference standard.

20. The ultrasonic inspection reference standard of claim 18, wherein said member is manufactured from a fiber-free photo-polymer resin.

21. The ultrasonic inspection reference standard of claim 15, wherein said reference standard is for the inspection of a fiber-reinforced composite part of an aircraft structure.

* * * * *